US005908631A

United States Patent [19]
Arnaud et al.

[11] Patent Number: 5,908,631
[45] Date of Patent: Jun. 1, 1999

[54] MONOHYDRIC ALCOHOL-FREE COMPOSITION FOR TOPICAL USE COMPRISING SOLUBILIZED ETHYLCELLULOSE

[75] Inventors: Pascal Arnaud, Creteil, France; Paul Thau, Berkeley Heights, N.J.

[73] Assignee: L'Oreal S.A., Clichy Cedex, France

[21] Appl. No.: 08/807,062

[22] Filed: Feb. 27, 1997

[51] Int. Cl.$^6$ .............................. A61K 6/00; A61K 7/00; A61K 7/04
[52] U.S. Cl. ............................................. 424/401; 424/61
[58] Field of Search .............................. 424/61, 64, 401, 424/474, 460, 464; 514/844, 871, 974

[56] References Cited

U.S. PATENT DOCUMENTS

| | | | |
|---|---|---|---|
| 2,230,063 | 1/1941 | Klimist | 167/85 |
| 4,151,304 | 4/1979 | Evans | 424/361 |
| 4,683,134 | 7/1987 | Palinczar | 424/59 |
| 4,686,099 | 8/1987 | Palinczar | 424/47 |
| 4,699,779 | 10/1987 | Palinczar | 424/59 |
| 4,749,574 | 6/1988 | Ueda et al. | 424/448 |
| 5,041,281 | 8/1991 | Strobridge | 424/59 |
| 5,100,655 | 3/1992 | Takano et al. | 424/63 |
| 5,288,482 | 2/1994 | Krzysik | 424/64 |
| 5,443,760 | 8/1995 | Kasprzak | 424/78 |
| 5,458,872 | 10/1995 | Durand | 424/59 |
| 5,462,729 | 10/1995 | Vlasblom | 424/61 |
| 5,462,737 | 10/1995 | Pleuger | 424/401 |
| 5,554,380 | 9/1996 | Cuca et al. | 424/441 |
| 5,656,278 | 8/1997 | Enjolras | 424/401 |

FOREIGN PATENT DOCUMENTS

| | | | |
|---|---|---|---|
| 0356325 | 2/1990 | European Pat. Off. | A61K 47/00 |
| 606608 | 1/1985 | Japan | A61K 7/025 |

OTHER PUBLICATIONS

L.C. Rutledge, et al., "Evaluation of Controlled–Release Mosquito Repellent Formulations," *Journal of the American Mosquito Control Association*, vol. 12(1), pp. 39–44 (1996).

V. Markina, et al., "Dynamics of Evaporation and Absorbability of Lotions and Creams Based on the Repellents DEET, Benzimine and Carboxide," *National Scientific and Research Institute for Disinfection and Sterilization at the U.S.S.R. Ministry of Health*, Moscow (Oct. 6, 1970), pp. 690–695.

C.D. Vaughan, "Using Solubility Parameters in Cosmetics Formulation," *J. Soc. Cosmetics Chem.*, vol. 36, pp. 319–333 (Sep./Oct. 1985).

Data Sheet for Brillance 515, Gatte fosee, Corporation, dated prior to Feb. 27, 1997.

Product Label for Origins Slip Cover—Estee Lauder, dated prior to Feb. 27, 1997.

J.M. Aiache et al., "New Gelification Method for Vegetable Oils I. Cosmetic Application," *International Journal of Cosmetic Science*, vol. 14, pp. 228–234 (1991).

Ethocel FP Polymers (DOW) Product Specification Sheet, printed in USA NMS11724 P.O. 63001526/Form No. 198–02001–1195GW, dated prior to Feb. 27, 1997.

*Chemical and Physical Properities of Hercules®–Ethylcellulose*, by Hercules Inc., pp. 1–44 (1989).

P. Gauthier et al., "Novel Glyceride Gels II. Viscosity Characteristics," *International Journal of Cosmetic Science*, vol. 18, pp. 229–235 (1994).

Christopher D. Vaughan, "Solubility Parameters for Characterizing New Raw Materials," *IFSC Conference*, vol. 108, pp. 57–63 Sep. 1993.

*Primary Examiner*—Johann Richter
*Assistant Examiner*—Sharon Howard
*Attorney, Agent, or Firm*—Baker & Botts, L.L.P.

[57] ABSTRACT

A monohydric alcohol-free composition for topical use on human lips and skin. The composition includes a commercialy acceptable carrier and solubilized ethylcellulose. The ethylcellulose is substantially solubilized in at least one solvent which may be a natural oil, a triglyceride, a propylene glycol ester, a neopentyl glycol ester, a fatty alcohol or mixtures thereof.

37 Claims, No Drawings

MONOHYDRIC ALCOHOL-FREE COMPOSITION FOR TOPICAL USE COMPRISING SOLUBILIZED ETHYLCELLULOSE

BACKGROUND OF THE INVENTION

This invention is directed to a monohydric alcohol-free composition comprising solubilized ethylcellulose. Particularly, this invention is directed to a monohydric alcohol-free composition for topical use on human lips and skin comprising a commercially acceptable carrier and solubilized ethylcellulose. The ethylcellulose being substantially solubilized in at least one solubilizing agent which may be a natural oil, triglyceride propylene glycol ester, neopentyl glycol ester, fatty alcohol or mixtures thereof. The solubilized ethylcellulose is present in a quantity sufficient to enhance the composition's adhesiveness and durability on the lips or skin to which the composition is applied.

The solubilizing agent of the present invention may be substituted or unsubstituted and may be saturated or unsaturated. Additionally the solubilizing agent may be a compound having a solubility parameter $\delta a$ and $\delta d$ within the following range:

$$15.00 (J/cm^3)^{1/2} \leq \delta d \leq 18.00 (J/cm^3)^{1/2}$$

$$8.00 (J/cm^3)^{1/2} \leq \delta a \leq 10.00 (J/cm^3)^{1/2}$$

wherein $\delta a = \sqrt{p^2 + \delta n^2}$.

The composition of the present invention may comprise more than one solvent to form a mixture of solvents. Said mixture of solvents has a solubility parameter $\delta a$ and $\delta d$ within the above-described range.

The invention is advantageous in that the use of the above-described solvent or solvents in combination with ethylcellulose in a cosmetic or pharmaceutical composition enables effective amounts of ethylcellulose to more easily be solubilized into the composition in the absence of monohydric alcoholic solvents, thereby forming improved formulations that are more tolerable by human skin or lips.

The present invention is also directed to a process for preparing cosmetic or pharmaceutical compositions comprising said monohydric alcohol-free composition comprising solubilized ethylcellulose.

Ethylcellulose is an ethyl ether of cellulose, and comprises a long-chain polymer consisting of anhydroglucose units joined together by acetal linkages. It has been observed that solubilized ethylcellulose functions as a hydrophobic film forming agent and a water-insoluble polymer component of cosmetic and pharmaceutical compositions. It has also been observed that inclusion of solubilized ethylcellulose in cosmetic or dermatological compositions enhances the adhesion, durability, viscosity and hydrophobicity efficacy of these compositions.

For instance, the inclusion of solubilized ethylcellulose in cosmetic and pharmaceutical compositions for lips and skin has been found to enhance the adhesion efficacy of such compositions, and hence minimize or alleviate undesirable migration beyond the areas to which these compositions were applied. The extent to which cosmetic or pharmaceutical compositions adhere to its intended surface is an important feature to consumers, particularly in lipstick, lip gloss, and other lip and skin care products.

Further, solubilized ethylcellulose has also been found to enhance the durability efficacy of cosmetic and pharmaceutical compositions applied to lips or skin, and hence improve the wearability of those compositions and may lessen or minimize undesirable transfer to items which may come into contact with the area of the skin or lip on which these compositions were applied. Additionally, solubilized ethylcellulose has also been found to minimize undesirable migration of cosmetics beyond those areas to which the cosmetic was applied, such as lips or a specific area of the skin. Because many compositions for lips and skin contain color and other stain causing agents, the minimization or elimination of undesirable transfer of these compositions is a significant feature to consumers. Solubilized ethylcellulose has further been observed to enhance water resistance, increase film formation on the skin and increase Skin Protection Factor (SPF) activity for sun screens.

However, ethylcellulose has very limited solubility in most solvents found in cosmetic and dermatological compositions. Typically, monohydric alcohols having about 2–8 carbon atoms, such as ethanol, butanol, methanol or isopropanol, are used to more easily solubilize effective amounts of ethylcellulose in a cosmetic or pharmaceutical composition. However, the drawback in using monohydric alcoholic solvents is that they are irritants and volatile, and consequently may be harmful to the skin after repeated use. There is, therefore, a need for a composition, more specifically a cosmetic or pharmaceutical composition, free of monohydric alcohols and having effective amounts of solubilized ethylcellulose contained therein.

Accordingly, it is one object of this invention to provide a composition adapted for topical use on human tissue which is free of monohydric alcohol yet enables substantially all of the ethylcellulose employed to be solubilized in said composition. This is advantageously accomplished by solubilizing the ethylcellulose using one or more of the following solvents, or mixtures thereof: natural oils, $C_6$–$C_{30}$ triglycerides, propylene glycol esters, neopentyl glycol esters, $C_{10}$–$C_{100}$ fatty alcohols, and compounds having a solubility parameter $\delta a$ and $\delta d$ within the following range:

$$15.00 (J/cm^3)^{1/2} \leq \delta d \leq 18.00 (J/cm^3)^{1/2}$$

$$8.00 (J/cm^3)^{1/2} \leq \delta a \leq 10.00 (J/cm^3)^{1/2}$$

wherein $\delta a = \sqrt{\delta p^2 + \delta n^2}$.

It is a feature of this invention that such compositions are useful in cosmetic applications such as compositions suitable for human lips or skin. Specifically, the lip cosmetic compositions of the present invention are long lasting and exhibit minimal undesirable migration above and below the lip line.

It is another feature of this invention that the compositions of the present invention are useful in pharmaceutical applications, including, but not limited to dermatological applications or compositions which may be used to deliver pharmaceutically effective ingredients via topical administration in humans or animals.

It is another object of this invention to provide a process for preparing such a monohydric alcohol-free composition. This process is accomplished by admixing ethylcellulose and the above-described solvent or solvents so that substantially all of the ethylcellulose is solubilized, while again advantageously avoiding the use of monohydric alcohols to achieve such solubilization. It is another feature of this invention that the process is useful in the preparation of cosmetic compositions. It is yet another feature of this invention that the process is useful in the preparation of pharmaceutical compositions.

It is yet another feature of this invention to provide a process that is useful in the preparation of compositions with improved adhesion and durability efficacies. It is yet another object of this invention to provide a method of enhancing the adhesion and durability of a composition on the lips or skin.

SUMMARY OF THE INVENTION

The present invention is directed to a monohydric alcohol-free composition for topical use on human tissue selected from the group consisting of lips and skin. The composition comprises a commercially acceptable carrier and solubilized ethylcellulose. The ethylcellulose is substantially solubilized in at least one solvent having a solubilization force sufficient to solubilize the ethylcellulose at a temperature of 80° C. to 100° C. The ethylcellulose is present in a quantity sufficient to contribute to the composition's adhesiveness and durability on the skin or lips to which the composition is applied.

In one preferred embodiment of the present invention, the composition comprises:

(a) from about 0.05% to about 20% by weight solubilized ethylcellulose; and (b) from about 10% to about 98% by weight of at least one solvent selected from the group consisting of natural oils, $C_6$ to $C_{30}$ triglycerides, propylene glycol esters, neopentyl glycol esters, $C_{10}$ to $C_{100}$ fatty alcohols, compounds having a solubility parameter $\delta a$ and $\delta d$ within the following range:

$$15.00 (J/cm^3)^{1/2} \leq \delta d \leq 18.00 (J/cm^3)^{1/2}$$

$$8.00 (J/cm^3)^{1/2} \leq \delta a \leq 10.00 (J/cm^3)^{1/2}$$

wherein $\delta a = \sqrt{\delta p^2 + \delta n^2}$, or mixtures thereof.

The composition of the present invention may also comprise more than one solvent, wherein the solubility parameter of said solvents together is within the range cited above for $\delta a$ and $\delta d$.

The composition is particularly useful as a cosmetic or pharmaceutical composition or component thereof.

The present invention is also directed to a process for preparing such a monohydric alcohol-free compositions comprising the steps of:

(a) providing from about 10–98% by weight of at least one solvent selected from the group consisting of natural oils, $C_6$–$C_{30}$ triglycerides, propylene glycol esters, neopentyl glycol esters, $C_8$–$C_{100}$ fatty alcohols, compounds having solubility parameters within the afore-cited range, and mixtures thereof; and (b) admixing the solvent with about 0.05–20% by weight of ethylcellulose.

The process is particularly useful in preparing cosmetic compositions and pharmaceutical compositions, including but not limited to, pharmaceutical compositions effective in treating or preventing disease or other damage to the skin or body.

The compositions of the present invention exhibit improved adhesion and durability efficacy in comparison to those compositions that contain no ethylcellulose. From these comparisons, it has been observed that solubilized ethylcellulose is an essential ingredient in improving adherence of cosmetic and pharmaceutical compositions on lips or skin, particularly in reducing undesirable migration beyond those areas to which the compositions were applied. Further, it has also been observed that solubilized ethylcellulose is an essential ingredient in improving durability of a cosmetic or pharmaceutical composition on lips or skin. It has also been observed that solubilized ethylcellulose reduces or minimizes undesirable migration of such compositions beyond the area to which they were applied. This feature is particularly useful in lip cosmetic compositions and compositions topically applied to the skin. In addition, the compositions of the present invention are free of monohydric alcohols, rendering such compositions more tolerable and less abrasive to the skin or lips after repeated use.

Accordingly, the present invention is also directed to a process of enhancing the adhesion and durability efficacy of a composition comprising the steps of:

(a) providing from about 10–98% by weight of at least one solvent selected from the group consisting of natural oils, $C_6$–$C_{30}$ triglycerides, propylene glycol esters, neopentyl glycol esters, $C_8$–$C_{100}$ fatty alcohols, compounds having solubility parameters within the afore-cited range, and mixtures thereof; and (b) admixing the solvent with about 0.05–20% by weight of ethylcellulose in the absence of a monohydric alcohol.

DETAILED DESCRIPTION OF THE INVENTION

It has been discovered that highly effective, non-irritating compositions comprising up to 20% solubilized ethylcellulose in the absence of monohydric alcoholic solvents are prepared by mixing ethylcellulose with natural oils, triglycerides, propylene glycol esters, neopentyl glycol esters, fatty alcohols and mixtures thereof. Additionally, the ethylcellulose may be solubilized in compounds having a solubility parameter $\delta a$ and $\delta d$ within the following range.

$$15.00 (J/cm^3)^{1/2} \leq \delta d \leq 18.00 (J/cm^3)^{1/2}$$

$$8.00 (J/cm^3)^{1/2} \leq \delta a \leq 10.00 (J/cm^3)^{1/2}$$

wherein $\delta a = \sqrt{\delta p^2 + \delta n^2}$.

For purpose of this invention, and as used in this specification and the appended claims, the term "monohydric alcohol" is defined as an alcohol having 2 to 8 carbon atoms and one hydroxyl functional group, such as ethanol, butanol, methanol or isopropanol. Accordingly, as used in this specification and the appended claims, the term "monohydric alcohol-free" refers to a composition which does not contain and specifically excludes the use of monohydric alcohols.

Ethylcellulose is a cellulose ether comprising a chain of beta anhydroglucose units joined together by acetal linkages. Each anhydroglucose unit has three replaceable hydroxyl groups, all or part of which may react as indicated by the following reaction:

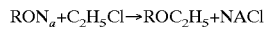

$$RON_a + C_2H_5Cl \rightarrow ROC_2H_5 + NACl$$

Complete substitution of all three hydroxyl groups would give each anhydroglucose unit a substitution value of 3 or ethoxyl content of 54.88%. The polymers of ethylcellulose which may be used in the present invention are preferably those polymers having a substitution value between 2.5 and 2.60 per anhydroglucose unite or 44 to 50% ethoxy content The present invention may contain from about 0.05% to about 20% by weight of ethylcellulose, based upon the total weight of the composition, in the absence of monohydric alcohol. The preferred amount of ethylcellulose is from about 0.05 to about 10% by weight of the total compositions Examples of ethylcellulose polymers suitable for use in the present invention include, but are not limited to, those manufactured by Dow Chemical Corporation (Midland, Mich.) and sold under the "ETHOCEL" trade name, including "ETHOCEL Standard 7 FP Premium" and "ETHOCEL Standard 100 FP Premium" (hereinafter "ETHOCEL 7 FP" and ETHOCEL 100 FP" respectively) The physical properties of these ethylcellulose polymers are set forth in Table I. Other commercially available ethylcellulose products suitable for use in this invention include those manufactured and sold by Hercules, Inc. (Wilmington, Del.) and referred to as "K-type", "N-type", and "T-type".

TABLE I

| Description | ETHOCEL 7 FP | ETHOCEL 100 FP |
|---|---|---|
| Viscosity at 25° with 5% (weight) of polymer in mixture of 20% ethanol and 80% toluene. The measure is effected using an ubhelodyde viscosimeter. | 6.0–8.0 cp | 90.0–110.0 cp |
| Ethoxyl Content | 48.0–49.5% | 48.0–49.5% |
| Particle Size, max. | 140 μm. | 150 μm. |
| Particle Size, mean | 5–15 μm. | 30–60 μm. |

The present invention also comprises a solvent capable of forming a homogenous system with ethylcellulose. The term "homogenous system" is defined herein to mean a system (e.g. liquid, solid, gel or gas) comprising ethylcellulose and the solvent, wherein the ethylcellulose is substantially or completely solubilized in the solvent The solvent of the present invention preferably has a solubilizing force sufficient to solubilize the ethylcellulose at a temperature of 80° C. to 100° C. For the purpose of this inventions and as used in this specification and appended claims, the term "solubilization force" is defined as the solvent's ability to substantially solubilize ethylcellulose while said solvent is at a specified temperature.

Suitable solvents for use in this invention are natural oils, triglycerides, propylene glycol esters, neopentyl glycol esters, fatty alcohols, compounds having a solubility parameter $\delta a$ and $\delta d$ within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2}$$

wherein $\delta a = \sqrt{\delta p^2 + \delta n^2}$, or mixtures thereof.

The present invention may contain from about 10% to about 98% by weight of such solvents individually or any combination thereof, based upon the total weight of the composition. The preferred total amount of solvent is about 60–95%, again based upon the total weight of the composition.

The natural oils suitable for use in the solvent component of the present invention include oils derived from plants and animals. Examples of such oils which are particularly preferred include castor oil, lanolin oil, castor oil and any derivatives thereof.

Triglycerides suitable for use in the solvent component of the present invention have from about 6 to 30 carbon atoms. Examples of suitable triglycerides which are particularly preferred include $C_8$–$C_{10}$ triglycerides, triheptanoin, triglycerides of caprylic and capric acids, such as capric triglyceride and caprylic triglyceride and mixtures thereof.

The propylene glycol esters which may be used as a solvent of the present invention include propylene glycol diesters of caprylic acid, capric acid or pelargonic acid. Examples of such compounds which are particularly preferred include propylene glycol dicaprylate, propylene glycol dicaprate, propylene glycol dipelargonate and mixtures thereof. Other preferred propylene alcohol esters for use in the present invention include propylene glycol diethylhexanoate and propylene glycol monoisostearate. Examples of neopentyl glycol esters suitable for use and preferred in the present invention include neopentyl glycol diethylhexanoate and neopentyl glycol diheptanoate and mixtures thereof Examples of other esters for use and preferred in the present invention include isostearyl lactate.

The fatty alcohols which may be used in the solvent component of the present invention have 10 to 100 carbon atoms, and may be branched or straight chain fatty alcohols. To the extent the fatty alcohol is a wax (i.e., solid) at ambient temperature, solubilization of the ethylcellulose may be accomplished at the melting temperature of such wax. Examples of suitable fatty alcohols which are preferred for use in the present invention include, oleyl alcohol octyldodecanol and mixtures thereof.

Compounds having a solubility parameter ($\delta a$ and $\delta d$) within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2}$$

wherein $\delta a = \sqrt{\delta p^2 + \delta n^2}$, may also be used as a solvent of the present invention.

Solubility parameters for compounds used in the cosmetic and pharmaceutical industry are listed in the *Cosmetic Bench Reference;* Carol Stream Ill., Allured Publishers (1992) and *The Handbook of Solubility Parameters and Other Cohesion Parameters,* 2nd Ed., Boca Raton, CRC Press (1992). The solubility parameter $\delta a$ and $\delta d$ of a compound may be determined by those having ordinary skill in the art.

Compounds falling within the above described range which may be used in the solvent component of the present invention are as follows:

| Compound | $\delta d(J/cm^3)^{1/2}$ | $\delta a(J/cm^3)^{1/2}$ |
|---|---|---|
| Castor oil | 16.79 | 9.09 |
| Propylene glycol monoisostearate | 16.36 | 8.74 |
| Isostearyl lactate | 16.36 | 8.74 |
| Oleyl alcohol | 16.28 | 8.17 |

In one embodiment of the present invention, the composition is a cosmetic composition. In another embodiment, the composition of this invention is a pharmaceutical composition.

Sun screens may be incorporated into the composition of this invention to at least partially block ultraviolet radiation from harming human skin. Organic sun screens for use in the cosmetic composition of this invention include any organic sun screen which absorbs, blocks or otherwise mitigates ultraviolet radiation. Without wishing to limit the invention in any way, such sun screen compositions include, but are not limited to, p-aminobenzoic acid, 2-ethoxyethyl-p-methoxy cinnamate, diethanolamine-p-methoxy cinnamate, digalloyl trioleate, 2,2-dihydroxy-4-methoxybenzophenone, ethyl-4-bis-(hydroxypropyl) aminobenzoate, 2-ethylhexyl-2-cyano-3,3-diphenyl acrylate, ethylhexyl-p-methoxy cinnamate, 2-ethylhexyl salicylate, glyceryl aminobenzoate, 3,3,5-trimethylcyclohexyl salicylate, lawson with dihydroxyacetone, menthyl anthranilate, 2-hydroxy-4-methoxy benzophenone, amyl-p-dimethylamino benzoate, 2-ethylhexyl-p-dimethylamine benzoate, 2-phenylbenzimidazole-5-sulphonic acid, red petrolatum, 2-hydroxy-4-methoxybenzophenone-5-sulphonic acid, triethanolamine salicylate, and the like. In additions suitable sun screens for use in the sun screen composition are set forth in Sunscreens Monogram, Federal Register, Vol. 58, No. 90, Proposed Rules, p. 28295 (May 12, 1993) Part B. Preferred sun screens for use in the invention are those manufactured under the PARSOL trade name such as PARSOL MCX, an octyl methoxycinnamate (OMC), and PARSOL 1789, both available from Givaudan Roure.

The present invention may comprise from about 2% to about 15% by weight of these sun screen agents or a mixture thereof. The preferred total amount of the sun screen agent is dependent on the SPF value desired to be obtained. Such amount may be ascertained by those skilled in the art.

The present invention may also comprise a silicone component such as a volatile cyclic silicone or a volatile short chain linear silicone, linear non-volatile silicone or mixtures of silicone fluids and ethylene oxide/propylene oxide silicone copolymers. An ethylene oxide/propylene oxide silicone copolymer component may be incorporated into the present invention to form oil-in-water or water-in-oil emulsions, to the extent there is water in the composition. The ethylene oxide/propylene oxide silicone copolymer is a surfactant. Examples of silicone components which may be used in the present invention include, but are not limited to, cyclomethicone, dimethicone, dimethicon silicone copolymers such as dimethicone copolyol and stearoxy dimethicone.

The present invention may further comprise from about 1% to about 45% by weight of these silicone components or a mixture thereof. The preferred total amount of silicone component is dependent on the product to be obtained and may be determined by those of ordinary skill in the art.

The present invention may further comprise one or more commercially acceptable carriers typically employed in cosmetic and pharmaceutical formulations as is well known to those skilled in the art. Such carriers may include emollients, surfactants, humectants and water. The total amount of such carrier may range from about 0.1% to 90% of the total weight of the composition. The type of carrier to be used is dependent on the product to be obtained and may be determined by those of ordinary skill in the art.

The cosmetic composition of this invention may also comprise other ingredients typically employed in cosmetic and pharmaceutical formulations, as is well known to those skilled in the art. For example, volatile components such as cyclomethicone or isododecane may be used in cosmetic compositions of the present invention, such as hair glosses, lip glosses, lipsticks, blusher and eye-shadow compositions. Such ingredients may also be employed in cosmetic and pharmaceutical compositions of the invention in dermatological gel vehicles. Such ingredients typically accelerate drying, reduce surface oiliness, and provide improved film formation. The present invention may contain from about 2% to 45% by weight of such volatile components.

The composition of the present invention above may be prepared by employing the following steps:

(a) providing from about 10–95% by weight of at least one solvent selected from the group consisting of natural oils, $C_6$–$C_{30}$ triglycerides, propylene glycol esters, neopentyl glycol esters, $C_8$–$C_{100}$ fatty alcohols, compounds having a solubility parameter δa and δd within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2}$$

wherein $\delta a = \sqrt{\delta p^2 + \delta n^2}$, and mixtures thereof; and (b) admixing the solvent with about 0.05–20% by weight of ethylcellulose, wherein the temperature is at about 80° C. up to about 100° C.

The method of this invention may also employ more than one solvent, wherein the solubility parameter of said solvents together is within the above-specified range for δa and δd.

In a particularly preferred embodiment of the method of this invention, the solvent is at a temperature of about 80–100° C. prior to admixture with the ethylcellulose. In another preferred embodiment, the solvent-ethylcellulose mixture is heated to maintain the temperature of the admixture at about 80–100° C. Admixture may be continued via mechanical or other means until substantially all of the ethylcellulose is solubilized. Admixture may also be continued with or without nitrogen pressure and may further be continued in an open or closed container.

The above method may be employed to prepare a cosmetic or pharmaceutical composition. The above process may also be employed to enhance the adhesion and durability efficacy of a composition, specifically cosmetic or pharmaceutical compositions such as those described herein.

The types of cosmetic and pharmaceutical compositions falling within the scope of the present invention may include, but are not limited to, lipsticks, lip glosses, hydrophobic pressed powder binders, hair glosses, hair conditioning agents, hydrophobic skin protectants, blushers, eye-shadows, sun screens, as well as pharmaceutical topical applications such as dermatological gel vehicles and the like.

The present invention also comprises a method of enhancing the adhesion and durability efficacy of a composition on human tissue, specifically lips or skin. Said method comprising applying to said tissue compositions which include as an ingredient thereof 10–98% by weight of any solvent described herein, and mixtures thereof, and 0.05 to 20% by weight of the ethylcellulose described herein, or mixtures thereof. Such compositions to be used in such a method include cosmetic or pharmaceutical compositions, including but not limited to those compositions described herein.

The following formulation examples are given to further illustrate the present invention. It is understood, however, that the invention is not limited to the embodiments disclosed herein. It is also understood that the invention may be practiced otherwise than as specifically illustrated and described without departing from its spirit or scope.

EXAMPLE 1

(Comparative Test)

Two monohydric alcohol-free lip rouge compositions illustrative of the present invention were formulated as follows:

| Component (control) | Formula A (% by weight) | Formula B (% by weight) |
|---|---|---|
| ETHOCEL 100 FP | 1.00% | — |
| Phase A | | |
| Castor oil | 23.15 | 23.15 |
| Octyldodecanol | 23.15 | 23.15 |
| Diisostearyl malate | 23.15 | 23.15 |
| Phase B | | |
| Lanolin | 10.88 | 11.85 |
| Polyethylene wax | 7.32 | 7.32 |
| Carnauba wax | 2.44 | 2.44 |
| Pigments | 8.44 | 8.44 |
| Preservatives | q.s.p | q.s.p |
| Fragrances | q.s.p. | q.s.p. |

The ETHOCEL 100 FP was mixed with Phase A constituents. After homogenizing at 95° C., the lanolin, waxes and pigments were added. After milling the pigments and adding the fragrance and preservatives, the lip rouge was poured into a mold of suitable shape for lipstick.

Formula A and Formula B were applied on half-lips to compare the adhesion properties of each formula. Specifically, migration of each formula above and below the lip line were compared. It was observed that Formula A, comprising solubilized ETHOCEL 100 FP, showed considerably less undesirable migration than Formula B, which contained no solubilized ETHOCEL. This comparative test evidenced that the inclusion of ethylcellulose in the composition improved adhesion efficacy and rendered such composition longer lasting than those containing no ethylcellulose.

EXAMPLE 2

ETHOCEL 100 FP was mixed with castor oil at 85–90° C. with moderate speed homo-mixing for four hours. The resulting 4% solution of ETHOCEL 100 FP had exceptional clarity in castor oil and formed a very high viscosity gel at room temperature.

The 4% Ethocel 100 FP/Castor Oil gel was applied to the lips and exhibited improved adhesion efficacy and film-forming properties by forming a dry, hydrophobic film on the lips after contact with moisture. The preferred concentration of ETHOCEL 100 FP in this embodiment is about 0.50% to 2.5%.

EXAMPLE 3

A monohydric alcohol-free formulation comprising 0.5. to 1.0% of ETHOCEL 7 FP in a castor oil base was compared to a comparative formulation containing no ethylcellulose.

It was observed that inclusion of 0.5% to 1.0% of ETHOCEL 7 FP in a castor oil lipstick base provided, (1) enhanced viscosity and cushion of the lipstick deposit on the lips; (2) improved "dry down" and adhesion efficacy to the lips; (3) increased hydrophobicity of the lipstick film; and (4) improved durability efficacy.

EXAMPLE 4

ETHOCEL 7 FP Premium was solubilized at a mass rate of 5% by dispensing it in one or more of the following solvent components at 100° C. with agitation:

Triheptanoin

Neopentyl glycol diheptanoate

Propylene glycol dipelargonate

Propylene glycol diethylhexanoate

Neopentyl glycol diethylhexanoate

Propylene glycol monoisostearate

Oleyl alcohol

Isostearyl lactate

Octyldodecanol

Castor oil $C_8$–$C_{10}$ propylene glycol diesters

Capric triglyceride and caprylic triglyceride

After the ETHOCEL 7 FP solubilized, the mixture was allowed to cool to room temperature. A partially translucent or transparent mixture was obtained, and remained stable at room temperature.

EXAMPLE 5

Two monohydric alcohol-free lip care cosmetic compositions illustrative of the present invention were formulated as follows

| COMPONENT | WEIGHT % |
|---|---|
| ETHOCEL 7 FP | 7.00 |
| Triheptanoin | 30.00 |

-continued

| COMPONENT | WEIGHT % |
|---|---|
| Castor oil | 26.00 |
| Capric triglyceride | 37.00 |
| and caprylic triglyceride | |
| | 100.00 |
| ETHOCEL 100 FP | 4.00 |
| Octyldodecanol | 75.60 |
| Octyldodecyl stearoyl stearate | 20.00 |
| Preservatives | q.p.s. |
| | 100.00 |

All the above constituents were weighed together and heated to 95° C. After homogenization, the mixture was allowed to cool to room temperature. This formulation resulted in an oily mixture suitable for application to the lips directly or over the film of lip rouge. When applied to the lips, the formulation enhanced the appearance of the lips of the wearer to whom the formulation was applied.

EXAMPLE 6

Two monohydric alcohol-free lip gloss compositions according to the present invention were formulated as follows:

| COMPONENT | WEIGHT % |
|---|---|
| ETHOCEL 7 FP | 5.00 |
| Phase A | |
| Castor oil | 28.00 |
| Octyldodecanol | 28.00 |
| Phenyl trimethicone | 28.00 |
| Phase B | |
| Polyethylene wax | 6.00 |
| Microcrystalline wax | 3.00 |
| Pigments, nacres | 2.00 |
| | 100.00 |

The ethylcellulose was mixed with the Phase A constituents at 95° C. After homogenizing the Phase B constituents were added, then the pigments and nacre. The mixture was poured into small pots and allowed to cool slowly to room temperature. This formulation resulted in a lip gloss formulation having improved adhesion and durability efficacy.

| COMPONENT | WEIGHT % |
|---|---|
| ETHOCEL 100 FP | 4.00 |
| Phase A | |
| Diisostearyl malate | 39.00 |
| Propylene glycol dicaprylate/dicaprate | 39.00 |
| Phase B | |
| Cyclomethicone | 10.00 |
| Phase C | |
| Pigments | 8.00 |
| | 100.00 |

The ETHOCEL 100 FP is mixed with the constituents of Phase A at 95° C. The pigments are then added and crushed Lastly, Phase B is added at 80° C. and the mixture is poured into a suitable tight receptacle.

The product may be applied to the lips with an applicator or a brush.

EXAMPLE 7

A monohydric alcohol-free lip rouge according to the present invention was formulated as follows:

| COMPONENT | WEIGHT % |
| --- | --- |
| ETHOCEL 7 FP | 5.00 |
| Phase A | |
| Castor oil | 20.00 |
| Octyldodecanol | 20.00 |
| Phenyltrimethicone | 20.00 |
| Phase B | |
| Lanolin | 15.00 |
| Polyethylene wax | 5.00 |
| Carnauba wax | 6.00 |
| Pigments | 8.00 |
| Preservatives q.s.p. | |
| Fragrances q.s.p. | |

The ETHOCEL 7 FP was mixed with Phase A constituents. After homogenizing at 95° C., the lanolin, waxes and pigments were added. After milling the pigments and adding the fragrance and preservatives, the lip rouge was poured into a mold of suitable shape for lipstick.

EXAMPLE 8

A monohydric alcohol-free non-transfer lip rouge according to the present invention was formulated as follows:

| COMPONENT | WEIGHT % |
| --- | --- |
| ETHOCEL 7 FP | 3.00 |
| Phase A | |
| Octyldodecanol | 25.00 |
| Phenyl trimethicone | 8.00 |
| Phase B | |
| Polyethylene wax | 15.00 |
| Pigments | 9.0 |
| Cyclomethicone | 40.00 |
| | 100.00 |

The ETHOCEL 7 FP was mixed with the Phase A constituents. After homogenizing at 95° C., the wax and pigments were added. After crushing the pigments and adding volatile silicone, the lip rouge was poured into a mold of suitable shape to produce a stick.

EXAMPLE 9

A monohydric alcohol-free water resistant sun screen gel according to the present invention was prepared as follows:

| | Wt. % |
| --- | --- |
| ETHOCEL 100 FP | 4.00 |
| Propylene Glycol Dicaprylate/Dicaprate | 33.00 |
| Dioctyl Malate (Ceraphyl 45-Van Dyk) | 45.00 |
| Octocrylene | 10.00 |
| PARSOL 1789 | 3.00 |
| Octyl Methoxycinnamate (OMC) | 5.00 |
| | 100.00 |

A clear, water resistant gel vehicle was obtained. The gel exhibited improved adhesion and durability efficacy.

EXAMPLE 10

A protective, moisturizing skin treatment gel according to the present invention was prepared as follows:

| | Wt. % |
| --- | --- |
| ETHOCEL 100 FP | 5.00 |
| Propylene Glycol Dicaprylate/Dicaprate | 30.00 |
| Dioctyl Malate | 30.00 |
| Cyclomethicone | 35.00 |
| | 100.00 |

A clear gel composition was obtained which formed a soft film on the skin after evaporation of the cyclomethicone. This gel may be used as a dermatological gel vehicle. Specifically, such a gel may be used to deliver pharmaceutically active agents to the skin or below the skins surface.

EXAMPLE 11

A high viscosity gel composition according to the present invention was prepared as follows:

| | Wt. % |
| --- | --- |
| ETHOCEL 100 FP | 18.50 |
| Propylene Glycol Dicaprylate/Dicaprate | 40.75 |
| Dioctyl Malate | 40.75 |
| | 100.00 |

After dissolution of the ETHOCEL in the solvents and cooling to room temperature, a rigid, clear gel was formed.

EXAMPLE 12

A dermatological vehicle composition according to the present invention was prepared as follows:

| | Wt. % |
| --- | --- |
| ETHOCEL 100 FP | 4.50 |
| Propylene Glycol Dicaprylate/Dicaprate | 30.50 |
| Dioctyl Malate | 15.00 |
| Isopropyl Hydroxy Stearate | 15.00 |
| Soy Sterol (Generol 122-Henkel) | 2.00 |
| Propylene Glycol | 2.00 |
| Cyclomethicone | 31.00 |
| | 100.00 |

A pharmaceutically active agent may also be employed in conjunction with this composition

EXAMPLE 13

A film forming hydrophobic skin protectant and skin gloss composition according to the present invention was prepared as follows:

| | Wt % |
| --- | --- |
| ETHOCEL 7 FP | 12.0 |
| Propylene Glycol Dicaprylate/Dicaprate | 26.5 |
| Dioctyl Malate | 26.5 |
| Cyclomethicone | 35.0 |
| | 100.00 |

We claim:

1. A composition adapted for topical use on human tissue selected from the group consisting of lips and skin, said composition comprising a commercially acceptable carrier and from about 0.05 to 20% by weight ethylcellulose, said ethylcellulose being solubilized in at least one solvent, wherein the at least one solvent comprises greater than 10 weight percent of the composition, and the composition is free of monohydric alcohol.

2. The composition according to claim 1, wherein the at least one solvent has a solubilization force sufficient to solubilize the ethylcellulose at a temperature from about 80° C. to 100° C. composition.

3. The composition according to claim 2, wherein the at least one solvent comprises lanolin oil.

4. The composition according to claim 2, wherein the at least one solvent comprises castor oil.

5. The composition according to claim 2, wherein the at least one solvent comprises a triglyceride selected from the group consisting of $C_8$ to $C_{10}$ triglycerides, triheptanoin, capric triglyceride, caprylic triglyceride and mixtures thereof.

6. The composition according to claim 2, wherein the at least one solvent comprises a propylene glycol ester selected from the group consisting of propylene glycol diethylhexanoate propylene glycol dicaprylate, propylene glycol dicaprate, propylene glycol dipelargonate and mixtures thereof.

7. The composition according to claim 2, wherein the at least one solvent comprises a neopentyl glycol ester selected from the group consisting of neopentyl glycol diheptanoate, neopentyl glycol diethylhexanoate and mixtures thereof.

8. The composition according to claim 2, wherein the at least one solvent is oleyl alcohol.

9. The composition according to claim 2, wherein the at least one solvent is octyldodecanol.

10. The composition according to claim 2, wherein the at least one solvent comprises isostearyl lactate.

11. The composition according to claim 2, wherein the at least one solvent comprises a compound having a solubility parameter δa and δd within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2},$$

wherein $\delta a = \sqrt{\delta p^2 + \delta n^2}$.

12. The composition according to claim 2, wherein said composition comprises more than one solvent, said solvents having a combined solubility parameter δa and δd within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2},$$

wherein $\delta a = \sqrt{\delta p^2 + \delta n^2}$.

13. The composition according to claim 2, wherein the composition is a pharmaceutical composition.

14. The composition according to claim 13, wherein the pharmaceutical composition is selected from the group consisting of sunscreen formulations, topical formulations, dermatological gel vehicles, hydrophobic skin protectants, water resistant gel vehicles or moisturizing skin treatment formulations.

15. The composition according to claim 2, wherein the composition is a cosmetic composition.

16. The cosmetic composition according to claim 15, wherein the cosmetic composition is selected from the group consisting of lipstick, lip gloss, lip rouge, hydrophobic pressed powder binder, hair gloss, hair conditioning agent, blusher and eye shadow.

17. A method of preparing a monohydric alcohol-free composition adapted for topical use on human tissue selected from the group consisting of skin or lips, said method comprising the steps of:

(a) providing from about 10–98% by weight of at least one solvent component, said at least one solvent component selected from the group consisting of: 1) lanolin oil; 2) triglycerides selected from the group consisting of $C_8$ to $C_{10}$ triglycerides, triheptanoin, capric triglycerides caprylic triglyceride and mixtures thereof; 3) propylene glycol esters selected from the group consisting of propylene glycol diethylhexanoate, propylene glycol dicaprylate, propylene glycol dicaprate, propylene glycol dipelargonate, and mixtures thereof; 4) neopentyl glycol esters selected from the group consisting of neopentyl glycol diheptanoate, neopentyl glycol diethylhexanoate and mixtures thereof; 5) $C_{10}$ to $C_{100}$ fatty alcohols selected from the group consisting of oleic alcohol, oleyl alcohol and mixtures thereof; 6) isostearyl lactate; and 7) mixtures thereof; and (b) admixing the solvent with about 0.05–20% by weight of ethylcellulose.

18. The method according claim 17, wherein said method is employed to enhance the adhesion efficacy of the composition.

19. The method according to claim 17, wherein said method is employed to enhance the durability efficacy of the composition.

20. The method according to claim 17, 18 or 19, wherein the solvent is at a temperature of about 80–100° C. prior to admixture with the ethylcellulose.

21. The method according to claim 17, 18 or 19, wherein the solvent-ethylcellulose admixture is heated to maintain the temperature of the admixture at about 80–100° C.

22. The method according to claim 17, 18 or 19, wherein admixing the solvent and ethylcellulose continues until all of the ethylcellulose is solubilized.

23. The method according to claim 17, 18 or 19, wherein the method is employed to prepare a cosmetic composition.

24. A method according to claim 17, 18 or 19, wherein the method is employed to prepare a pharmaceutical composition.

25. A method according to claim 17, 18 or 19, wherein the at least one solvent is a compound having a solubility parameter δa and δd within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2},$$

wherein $\delta a = \sqrt{\delta p^2 + \delta n^2}$.

26. A method of enhancing the adhesion efficacy of a monohydric alcohol-free composition on human tissue selected from the group consisting of lips and skin; said method comprising applying to said tissue the composition which includes as an ingredient thereof:

(a) from about 0.05–20% by weight ethylcellulose; the ethylcellulose being substantially solubilized in at least one solvent selected from the group consisting of: 1) lanolin oil; 2) triglycerides selected from the group consisting of $C_6$ to $C_{30}$ triglycerides, triheptanoin, capric triglyceride, caprylic triglyceride and mixtures thereof; 3) propylene glycol esters selected from the group consisting of propylene glycol diethylhexanoate, propylene glycol dicaprylate, propylene glycol dicaprate, propylene glycol dipelargonate and mixtures thereof; 4) neopentyl glycol esters selected from the group consisting of neopentyl glycol diheptanoate, neopentyl glycol diethylhexanoate and mixtures thereof; 5) oleyl alcohol; 6) isostearyl lactate; and 7) mixtures thereof; and (b) said solvent comprising 10–98 weight percent of the total weight of the composition.

27. The method according to claim 26, wherein said method is employed to enhance the durability efficacy of a monohydric alcohol-free composition on said human tissue selected from the group consisting of human skin and lips.

28. The method according to claim 26 or 27, wherein the at least one solvent is a compound having a solubility parameter δa and δd within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2},$$

wherein $\delta a = \sqrt{\delta p^2 + \delta n^2}$.

29. The method according to claim 26 or 27, wherein said method employs more than one solvent, said solvents having a combined solubility parameter δa and δd within the following range:

$$15.00(J/cm^3)^{1/2} \leq \delta d \leq 18.00(J/cm^3)^{1/2}$$

$$8.00(J/cm^3)^{1/2} \leq \delta a \leq 10.00(J/cm^3)^{1/2},$$

wherein $\delta a = \sqrt{\delta p^2 + \delta n^2}$.

30. The method according to claim 26 or 27, wherein the composition is a cosmetic composition.

31. The method according to claim 26 or 27, wherein the composition is a pharmaceutical composition.

32. The composition according to claim 30, wherein the pharmaceutical composition is selected from the group consisting of sunscreen formulations, topical formulations, dermatological gel vehicles, hydrophobic skin protectants, water resistant gel vehicles or moisturizing skin treatment formulations.

33. The method according to claim 30, wherein the cosmetic composition is selected from the group consisting of lipstick, lip gloss, lip rouge, hydrophobic pressed powder, hair gloss and hair conditioning agent, blusher and eye shadow.

34. The method according to claim 26 or 27, wherein said at least one solvent is selected from the group consisting of castor oil, propylene glycol monoisostearate and mixtures thereof.

35. The method according to claim 26 or 27, wherein said at least one solvent is octydodecanol.

36. The method according to claim 17, 26 or 27, wherein the at least one solvent is castor oil.

37. The method according to claim 17, 26 or 27, wherein the at least one solvent is octydodecanol.

* * * * *